United States Patent
Tong et al.

(10) Patent No.: US 10,603,230 B2
(45) Date of Patent: Mar. 31, 2020

(54) LOW FRICTION CORE-SHELL NANOFIBROUS MEMBRANES FOR DELIVERY OF ACTIVE INGREDIENTS TO THE WET SKIN

(71) Applicant: Nano and Advanced Materials Institute Limited, Hong Kong (HK)

(72) Inventors: Ho Wang Tong, Hong Kong (HK); Connie Sau Kuen Kwok, Hong Kong (HK)

(73) Assignee: Nano and Advanced Materials Institute Limited, Hong Kong (HK)

( * ) Notice: Subject to any disclaimer, the term of this patent is extended or adjusted under 35 U.S.C. 154(b) by 147 days.

(21) Appl. No.: 15/788,777

(22) Filed: Oct. 19, 2017

(65) Prior Publication Data
US 2018/0125729 A1    May 10, 2018

Related U.S. Application Data

(60) Provisional application No. 62/497,077, filed on Nov. 9, 2016, provisional application No. 62/497,078, filed on Nov. 9, 2016.

(51) Int. Cl.
*A61F 13/511* (2006.01)
*D01D 5/34* (2006.01)
(Continued)

(52) U.S. Cl.
CPC .. *A61F 13/51113* (2013.01); *A61F 13/15617* (2013.01); *A61F 13/49* (2013.01); *A61F 13/51121* (2013.01); *A61L 15/44* (2013.01); *A61L 15/60* (2013.01); *D01D 5/0038* (2013.01); *D01D 5/0046* (2013.01); *D01D 5/0069* (2013.01); *D01D 5/34* (2013.01); *D01F 1/10* (2013.01); *D01F 2/00* (2013.01); *D01F 6/90* (2013.01); *D01F 8/12* (2013.01); *D04H 1/728* (2013.01); *A61F 2013/00906* (2013.01); *A61F 2013/15097* (2013.01); *A61F 2013/15235* (2013.01); *A61F 2013/15447* (2013.01); *A61F 2013/15934* (2013.01); *A61F 2013/49098* (2013.01); *A61F 2013/5103* (2013.01); *A61F 2013/51117* (2013.01); *A61F 2013/530306* (2013.01); *A61L 2400/12* (2013.01); *D10B 2201/02* (2013.01); *D10B 2401/022* (2013.01);
(Continued)

(58) Field of Classification Search
USPC ................................... 442/346, 347
See application file for complete search history.

(56) References Cited

U.S. PATENT DOCUMENTS

2012/0077405 A1 * 3/2012 Zhou .................. D01D 5/00
442/346

OTHER PUBLICATIONS

Jan D. Bos et. al., "The 500 Dalton rule for the skin penetration of chemical compounds and drugs", Experimental Dermatology, 2000, 9, p. 165-169.

* cited by examiner

*Primary Examiner* — Lynda Salvatore
(74) *Attorney, Agent, or Firm* — Idea Intellectual Limited; Margaret A. Burke; Sam T. Yip

(57) ABSTRACT

A membrane for skin comprising a plurality of randomly oriented core-shell nanofibers is provided in the present invention, where each of said core-shell nanofibers comprises at least an active-ingredient-loaded polymeric core and a non-polymeric shell consisting of active ingredients only surrounding the core. Related fabrication method of said membrane is also provided in the present invention.

18 Claims, 11 Drawing Sheets

(51) Int. Cl.
*D01F 1/10* (2006.01)
*D01D 5/00* (2006.01)
*D04H 1/728* (2012.01)
*A61F 13/15* (2006.01)
*A61F 13/49* (2006.01)
*A61L 15/44* (2006.01)
*A61L 15/60* (2006.01)
*D01F 2/00* (2006.01)
*D01F 6/90* (2006.01)
*D01F 8/12* (2006.01)
*A61F 13/00* (2006.01)
*A61F 13/51* (2006.01)
*A61F 13/53* (2006.01)

(52) U.S. Cl.
CPC .............. *D10B 2403/0241* (2013.01); *D10B 2403/0242* (2013.01); *D10B 2509/026* (2013.01)

LOW FRICTION CORE-SHELL NANOFIBROUS MEMBRANES FOR DELIVERY OF ACTIVE INGREDIENTS TO THE WET SKIN

CROSS-REFERENCE TO RELATED APPLICATIONS

This application is a non-provisional application claiming priorities from the U.S. provisional patent application Ser. No. 62/497,077 filed on Nov. 9, 2016 and the U.S. provisional patent application Ser. No. 62/497,078 filed on Nov. 9, 2016, and the disclosure of which are incorporated herein by reference in their entirety.

FIELD OF INVENTION

The present invention relates to nanofibrous membranes capable of delivering one or more active ingredients in a controlled release manner. In particular, it relates to nanofibrous membranes that have a core/shell nanofibrous structure where the shell solely contains active ingredient and is highly dissolvable while the core is a polymeric matrix incorporated with one or more active ingredients which is relatively less dissolvable when they are in contact with a wet surface such as human skin. The present invention also relates to methods of fabricating the nanofibrous membranes.

BACKGROUND

Importance of Skincare

Human skin acting as protective barrier for human body is continuously under exposure of internal and external causes that affect its condition and functioning. The external causes are primarily environmental factors, such as ultraviolet (UV) irradiation, free radicals, pollution and dirt in the air, toxic and allergic compounds, and mechanical damage. Endogenous factors might be some genetic predisposition, immune and hormone disorder, stress and lack of sleep and internal aging process. Consequently, skin exposed to these conditions could undergo slow deterioration over time as the daily damaging effects could gradually accumulate and eventually lead to a series of skin disorders such as skin irritation, allergy, pigmentation, wrinkling and dryness.

Dietary complementation with the essential skin care products could improve skin conditions. These skin care products could be in the form of toner, lotion, cream, paste, peeling-off, powder, gel or sheet with active ingredients loaded that directly altered skin appearance. The active ingredients include but not limited to vitamins, minerals, essential fatty acids, peptides, polymers, antioxidants, organic acid, and plant extracts which possess the function of skin moisturization and hydration, anti-acne, anti-irritation whitening, and prevention of aging. The active ingredients could be single component or mixture of components. For example, active ingredients for hydration function such as hyaluronic acid, petroleum could form a protective layer on skin surface to preventing water loss as, while as some chemical compounds such as glycerol, natural moisturizing factors (NMF) is able to absorb water within the air and maintain the moisturization level of the skin. Some active ingredients such as vitamin C could stimulate the formation of collagen to prevent wrinkle formation, and inhibit the tyrosinase activity and melanine pigmentation formation to whitening the skin. Some active ingredients such as antioxidants could directly decrease the amount of reactive oxygen species (ROS) in skin cells thus thwart oxidative stress, thereby preventing aging phenomenon.

Skincare is also critical for sanitary products such as diapers and sanitary napkins. Minimal rewet is desirable for these products such that complications such as diaper rash can be minimized.

Skincare Using Membranes for Delivery of Active Ingredients to Skin

Generally speaking the skincare mask or skin care membrane or transdermal patch could be defined as a subject which can be applied on the surface of skin for benefiting skin appearance and improve the condition of skin. Depending on the location applied, the skincare mask could be but not limited to facial mask, eye mask, hand mask, lip mask and neck mask. The form of skincare masks could be but not limited to paste, powder, gel, membrane and sheet. Based on its moisturizing condition, skincare masks could be mainly divided into two types: (1) dry type that does not contain any water; and (2) pre-moistened type that is fully loaded with nutrient solutions and functional ingredients. The latter is the most common type which occupies the most shares of current market, whereas the former is not very popular probably because of the inconvenience for usage.

Typical pre-moistened skin masks are generally composed of sheet materials carrying the following components: water, active ingredients, preservatives, water-thickening agents, plant extracts, soothing components, pH balancers, stabilizers, and fragrance ingredients. Among all these components, only the active ingredients are the contents that directly interact with skin for enhancing skin appearance and improving skin conditions. The functions of all the other components are to maintain the quality and stability of the skin masks. For example, the function of preservatives is to inhibit the bacteria growth as the moistened condition is prone to the formation of bacteria colony. The water-thickening agent is to increase the viscosity of the solution within the skin mask so that the solution will not flow elsewhere and stay within the skin mask applied area. Plant extracts and fragrance ingredients were usually used to attract consumers with pleasant smell and the usage of natural ingredients. Soothing component is to reduce the feeling of irritation caused by the filtration of active ingredients into skin. PH balancer is to adjust the pH of pre-moistened skin mask for optimal skin use whereas stabilizer is to maintain the chemical stability of the components within skin masks.

Dry skin masks are usually in the form of powder or dry membranes or dry sheets. Dry skin masks do not contain any water. The usage of dry skin masks requires pre moisturization procedure. Dry skin masks do not contain preservatives, water-thickening agents, pH balancers, and stabilizers. Consequently dry skin masks significantly reduce the risk of skin allergic reaction, skin sensitive issues and some side effects caused by preservatives and other chemicals.

Delivery of active ingredients via transdermal path is primarily limited by skin's outermost layer called stratum corneum (SC), which is 10 to 20 µm thick. The SC layer is composed of non-living corneocyte cells with cross-lined keratin and a mixture of intercellular lipids forming a brick and mortar structure. Only small molecules and lipids can diffuse through the skin barrier and transport across the stratum corneum. The size of the molecule which is tied to its molecular weight is an important factor that determined its penetration efficiency. Most molecules are too large to make its way through the skin. According to the 500 Dalton rule for skin penetration of chemical compounds and drugs, anything smaller than 500 Daltons can penetrate skin whereas anything larger than 500 Daltons cannot. (Bos, Jan D., and Marcus MHM Meinardi. "The 500 Dalton rule for the skin penetration of chemical compounds and drugs." *Experimental dermatology* 9.3 (2000): 165-169.)

Different Types of Membranes for Delivery of Active Ingredients to Skin

Typical sheet-materials for pre-moistened masks on the market are generally made of non-woven sheets. The materials of the non-woven sheets include but not limited to polypropylene (PP), polyethylene terephthalate (PET), cotton, plant pulp, lyocell fiber, tencel fiber, biocellulose, rayon/viscose, and natural silk. The cost of non-woven sheet is low and its mechanical strength is high, though its limitations include poor skin contact and low absorbency. Furthermore, the polymers could cause sensitive skin. Therefore, this type of materials gradually diminished from the market. Cotton still occupies a certain share of skin mask market probably because of its low possibility of causing skin allergic reactions. But their disadvantage is its poor skin contact. Lyocell (Tencel) fiber was produced from pulp fibers. Therefore, it shares the same cellulosic properties with cotton but it is more soft and absorbent than cotton probably because of its special manufacturing technique.

The concept of nanofiber as skin mask materials has been proposed for over 30 years. The nanostructure rendered its excellent skin contact property. Active ingredients could be easily co-electrospun into the fiber and no preservative is needed for the final dry product. Furthermore, the excellent skin contact further leads to superior penetration of active ingredients of the mask. Various patents based on nanofibers for cosmetic purpose have been filed in recent years. (Tojo, Takehiko, and Masataka Ishikawa. "Method for attaching nanofiber sheet." U.S. Patent Application Publication No. US2011/0256397. Tojo, Takehiko, Masataka Ishikawa, and Yoshimi Yamashita. "Nanofiber sheet." U.S. Pat. No. 8,642,172. 4 Feb. 2014. Tojo, Takehiko, and Masataka Ishikawa. "Nanofiber laminate sheet." U.S. Patent Application Publication No. US2013/0122069. Golubovic-Liakopoulos, Nevenka, Bhavdeep Shah, and Erik Andersen. "Compositions and methods for the delivery of agents." U.S. Pat. No. 9,233,080. 12 Jan. 2016. Kim, Chan. "Cosmetic sheet formed from nanofiber with controlled dissolution velocity and method of manufacturing the same." U.S. Patent Application Publication No. US2015/0272855. Smith, D., et al. "Electrospun skin masks and uses thereof." PCT Int. Appl Publication No. WO 2001026610 A1 (2001): 14. Kusukame, Haruka, Tomoki Masuda, and Masayo Shinoda. "Method of producing an adhesive sheet for skin, cosmetic method and adhesive sheet for skin." U.S. Patent Application Publication No. US2015/0265030. Nishio, Toshihiko, et al. "Water-soluble electrospun sheet." U.S. Patent Application Publication No. US2010/0254961. Glenn VILE, Iain Cameron HOSIE, Simon Vaughan FEASEY. Bioactive nanofibres WO 2013035072 A1. Bo-Kyung Choi, Ji-Hwa Lee. Mask pack WO 2013078094 A1. Tom Sekiguchi, Aiko Watanabe, Yu Watanabe. A cosmetic sheet WO 2014125407 A1. Chen, Fung-Jou, Lei Huang, and Jeffrey Lindsay. "Gradient nanofiber materials and methods for making same." U.S. Patent Application Publication No. US2006/0094320.) The disclosure of any patent and non-patent literatures cited herein are incorporated by reference in their entirety.

The above patents disclosed active ingredient-loaded nanofibers or nanofiber composites consisting of both nanofibers and other types of membranes or sheets. The disclosed nanofibers could be water dissolvable or non-dissolvable or semi-dissolvable by combining different type of nanofibers. The details are described as follows:

(1) Water-Soluble Sheet

Nishio et al. disclosed a water-soluble electrospun sheet consisting of high-molecular base materials and functional ingredients. Kim et al. disclosed a cosmetic sheet comprising water-soluble nanofibers with controlled dissolution velocity. Glenn et al. disclosed a dissolvable web structure article comprising active ingredients. Choi et al. disclosed a mask pack including a non-woven fabric layer and a nanofiber layer comprising a hydrophilic polymer.

(2) Laminated Sheet

In this category, the skin mask is composed of several different laminated layers. For example, Tojo et al. disclosed a nanofiber sheet containing a water-soluble adhesive component, a water-insoluble nanofiber layer and a base layer.

(3) Water-Insoluble Composite

Golubovic-liakopoulos et al. disclosed a composite formed by different type of nanofibers containing hydrophobic nanofiber and hydrophilic nanofibers, which intertwined together to form one single layer for delivery of cosmetic active ingredients. Chen et al. disclosed gradient nanofiber composites comprising several different types of nanofibers. Kusukame et al. disclosed an adhesive sheet by attaching a water-absorptive support to a water-permeable film delivering functional ingredients.

Shortcomings of the Prior Art

However, none of these nanofiber patents disclosed the distinctive physical properties of nanofibers such as the structure of nanofibers, the mechanical strength and the release property. These properties strongly affect the performance of nanofibers for skincare application. Furthermore, the water dissolvable nanofiber skin mask does not solve the poor skin contact problem. Poor skin contact will further lead to poor penetration of ingredients due to limited contact points between the mask and skin. The handling property is another concern of water-insoluble nanofiber skin mask. The electrospun membrane is very thin. When applied to the pre-moistened skin, it is easy to be ruptured when stretched during the using procedure. Moreover, it is very hard for them to move along the skin surface for best position adjustment due to large friction force between skin and the mask. As a result, there exists a need for nanofiber skin mask with good handling property as well as excellent skin contact.

SUMMARY OF INVENTION

One objective of this invention is to provide a low friction membrane capable of delivering active ingredients to the wet skin in a controlled release manner. The membrane is composed of a plurality of randomly oriented core-shell nanofibers. A schematic diagram of the core-shell nanofiber according to an embodiment of the present invention is shown in FIG. 1. Each of the core-shell nanofibers (100) comprises at least a polymeric core (101) and a non-polymeric shell (102). The nanofiber shell, namely, an "instant release" or "rapid release" shell, is mainly composed of one or more active ingredients such as small molecules for skincare. The "instant release" shell remains intact under a dry condition but it can be dissolved instantly under a wet condition, for instance, when applied to the wet skin. The nanofiber core, namely, a "controlled release" core, is an active ingredient-incorporated nanofiber. The "controlled release" core remains intact under either a dry or wet condition because the core comprises one or more polymers incorporated with one or more active ingredients.

The present membrane is useful in nanofiber skin mask which includes but not limited to facial mask, eye mask, hand mask, lip mask, neck mask or any mask thereof.

Uniqueness

In the prior arts, most core-shell nanofibers are composed of a polymeric core and a polymeric shell. The present core-shell nanofibers, on the other hand, are composed of an active ingredient-loaded polymeric core and a polymer-free shell consisting of active ingredients only. The active ingredients such as small molecules can not only be attracted to the polymer core but also attracted to each other via hydrogen bonding or electrostatic attraction, provided that the selected active ingredients and the polymer core material have functional groups, or the selected polymer core material and the selected active ingredients exhibit sufficient charge-bearing ability.

In most prior arts, the polymeric core is loaded with drugs or bioactive molecules while the polymeric shell is used to protect the drugs or bioactive molecules in the core. In some of those prior arts, the polymer shell is used to control the release of drugs or bioactive molecules from the core. In contrast, the present shell is composed of active ingredients that can be dissolved instantly when moisturized or hydrated (200). The shell can become a layer of highly concentrated solution (102') when moisturized or hydrated such that the mobility of the core on the surface can be significantly enhanced, resulting in a "low friction" nanofiber (100') with respect to the skin surface that the core (101) is subsequently interfaced with after the shell is dissolved (an example is shown in FIG. 2).

It can be found in the prior arts that the core-shell nanofibers can be made by forming the nanofiber core first, followed by various surface modification strategies to form the nanofiber shell. These strategies include conjugation of drugs on the polymer matrix of the core, post-electrospinning coating, plasma treatment, and their combination thereof. However, in these prior arts, the core-shell nanofibers cannot be made through a one-step process. Therefore, another objective of the present invention is to provide a one-step process for making core-shell nanofiber of the low friction membrane of the present invention. Briefly, the present one-step fabrication method comprises dissolving selected polymer and selected active ingredients into an appropriate solvent to form a solution, which is then processed into nanofibers via free-surface electrospinning. It should be noted that the term "free-surface" and "needleless" are used interchangeably throughout the present application to define that the electrospinning used in the present method is without any needles but is still able to fabricate the present nanofiber with a polymeric core and non-polymeric shell in one step, devoid of any post-electrospinning coating or post-treatment.

Advantages

Since the shell can become a layer of highly concentrated solution when moisturized, when the membrane is applied to the skin, the friction at the interface of the membrane and the outer layer of the skin can be significantly reduced, resulting in an excellent mobility of the membrane on the skin. This feature is especially advantageous when the membrane is used as a skin mask such as a facial mask because the user usually fails to apply the mask to the desired position at the first time, meaning that further adjustment is usually required. If the friction at the membrane-skin interface is high, the membrane is often significantly wrinkled during adjustment, thus affecting the skin contact. The low friction feature of the membrane described in the present invention can ensure good mobility of the membrane during adjustment, thus preventing formation of wrinkles and providing excellent skin contact even after multiple adjustments.

The excellent skin contact can enhance skin penetration of the ingredients, which is a critical feature when it comes to skin mask application.

As the ingredients are incorporated with the nanofibers in a dry condition, enhanced stability of the ingredients is expected when compared with the conventional skin masks soaked in essence.

It is also worth noting that the present invention is preservative-free, which is virtually impossible for most commercial skin masks soaked in essence.

The core-shell nanofibers can also minimize the rewet when applied to the superabsorbent polymer of sanitary products such as diapers and sanitary napkins as a layer of top sheet. Due to multiple channels of the core-shell nanofibers, the fluid such as urine can be relocated quickly to difficult-to-reach location of the superabsorbent polymer, thus minimizing the rewet of the sanitary product comprising the said nanofibers.

Methodology

The present membranes are fabricated by preparing a special formulation, followed by a modified electrospinning process. An embodiment of the present fabrication process/method is shown in FIG. 3.

Briefly, one or more selected active ingredients are mixed with a polymer solution to form a mixture and the mixture [namely, active ingredients in polymer solution (Solution A)] is loaded into a reservoir (301) capable of moving back and forth through an electrode at high voltage (302) such that the electrode is coated with the said mixture. An active ingredient solution [namely, active ingredients in aqueous solution (Solution B)] is loaded into the same reservoir simultaneously such that the electrode is coated with both Solution A and Solution B, which is a unique electrospinning process. A moving substrate (303), which is grounded, is placed at a certain distance above the electrode (302) such that an electric potential difference (304) is created between the electrode (302) and the substrate (303). As further illustrated in FIG. 4, when the solutions are coated onto the electrode (401), an electric force is applied to the solutions (402). After that, multiple cone-like structures (402a) are formed along the electrode due to the interaction between the electric force applied to the solutions and the surface tension of the solutions. When the electric force overcomes the surface tension (403), a polymer jet (404) is initiated from each cone-like structure. The polymer jet is a coaxial structure (404) comprising an active ingredient-loaded polymer solution core (404a) and an active ingredient solution shell (404b) surrounding the core. After solvent evaporation, the polymer jet solidifies and becomes core-shell nanofibers, which are collected on the moving substrate. When the amount of active ingredients is sufficiently high, a layer of active ingredients is formed on the polymer core after electrospinning, provided that the active ingredients possess functional groups for hydrogen bonding or the active ingredients possess sufficient charges. The layer of active ingredients serves as a shell surrounding the core.

The core-shell structure of each nanofiber of the membrane can be confirmed by using SEM to examine the fiber structure before and after soaking the membrane in water. The core-shell structure can also be confirmed by examining the core-shell nanofibers using TEM. The performance of the invented membranes is evaluated in various aspects including but not limited to handling property, ingredient stability, mobility when applied to wet skin, and skin penetration.

The active ingredients include but not limited to proteins, peptides and small molecules. In particular, the small molecules can possess various skincare functions such as hydration/moisturizing function, acne treatment, anti-irritation, whitening, anti-aging, or anti-oxidant. The small molecule for hydration/moisturizing function can be urea, pyrrolidone carboxylic acid (PCA), panthenol, trehalose, cyclomethicone, caprylyl glycol, lecithin, tocopheryl acetate, squalane, hydrolysed collagen, polyquaternium-51 or methyl gluceth-20. The small molecule for acne treatment can be alpha hydroxyl acid (AHA), salicylic acid, menthol or niacinamide. The small molecule for anti-irritation can be allantoin, bisabolol or dimethicone. The small molecule for whitening can be ascorbic acid, kojic acid, hydroquinone, azelaic acid or niacinamide. The small molecule for anti-aging can be vitamin E or retinoic acid. The small molecule for anti-oxidant can be resveratrol, epigallocatechin-3 gallate (EGCG), lycopene, genistein, trehalose.

The polymer can be nylon, cellulose acetate (CA), polystyrene (PS), polyacrylonitrile (PAN), poly(lactic acid) (PLA), poly(lactic-co-glycolic acid) (PLGA), polybutylene terephthalate (PBT), polyurethane (PU), gelatin, chitosan or polyhydroxybutyrate-co-hydroxyvalerate (PHBV).

The present invention relates to a novel method of producing core-shell nanofibers, core-shell sub-micron fibers and core-shell microfibers for transdermal delivery of active ingredients. The present method renders greater flux of active ingredients release in a very fast manner (seconds to minutes). In addition, the core of the fibers remains intact and forms a lotus effect on skin, which further enhances the penetration of the active ingredients into the skin. The active ingredients could not only be cosmetic agents but also medicines that could be delivered into the skin via transdermal pathway. In preferred embodiments, the invention relates to the delivery of vitamins, peptides, small molecules and other bioactive compounds, whether alone, in mixtures, in combination with other carriers or agents, or in encapsulated form using the compositions and methods disclosed herein. In further embodiments, the invention relates to compositions comprising drugs such as paracetamol, which can be released instantly for alleviating pain, symptoms, diseases and disorders, and/or for treatment thereof, through transdermal delivery of pharmaceuticals.

The present invention contemplates films or patches or masks wherein the active ingredients occupy the major components (greater than 50%, more preferably at least 70%, still more preferably at least 80%), and substantially all the active ingredients are delivered. In contrast, the traditional skin mask or skin patch only contains a small portion of active ingredients (1-10%) and only a small percentage of active ingredients could be released due to the retention property of the materials used in the traditional skin mask. Furthermore, the present invention provides a skin mask or membrane or patch that carries active ingredients without any other softeners, stabilizers and preservatives.

In general, the present invention provides a skin mask comprising the fibrous membrane made of the plurality of electrospun fibers fabricated according to certain embodiments of the present invention for improving skin condition.

A method of forming the skin mask comprises the steps of electrospinning the plurality of fibers according to certain embodiments of the present invention and directly assembling the electrospun fibers onto a substrate in the form of a skin covering or mask. For those fibers containing active ingredients, the ingredients may leach, diffuse, or be otherwise transferred to the skin once interacting with the water on the pre-moistened skin. After the ingredients have performed their function(s), the covering or mask may be removed by peeling or other removal methods from the skin.

The skin mask described herein above can be formed using free-surface electrospinning and methods that can provide for free-surface electrospinning of fibrous coating comprising core-shell nanofibers, core-shell microfibers, core-shell submicron fibers, core-shell fibers interlaced with non-core-shell fibers or the combination thereof.

The solution or emulsion or suspension or dispersion for free-surface electrospinning can include one or several selected active ingredients and one or several selected polymers.

The electrospun fibers can bear electrostatic charges.

In an example, the present invention provides a skin mask comprising the low friction core-shell structured microfibers.

In another example, the present invention provides a skin mask comprising the low friction core-shell structured submicron fibers.

In another example, the present invention provides a skin mask comprising the low friction core-shell structured nanofibers.

This Summary is intended to provide an overview of the present invention, and is not intended to provide an exclusive or exhaustive explanation.

DETAILED DESCRIPTION OF INVENTION

Figure 1:
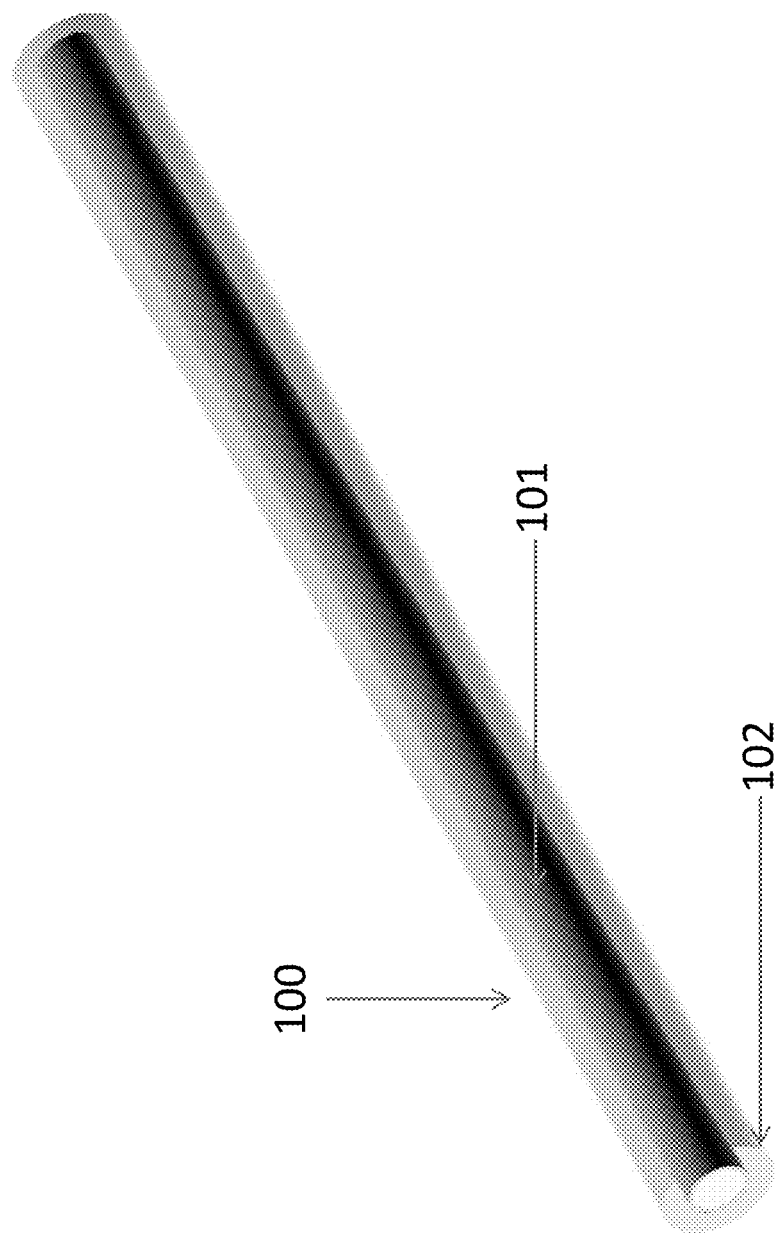
FIG. 1 is a schematic diagram of core-shell nanofiber consisting of an active ingredient-loaded polymer matrix core and a layer of active ingredient shell surrounding the core.
Figure 2:
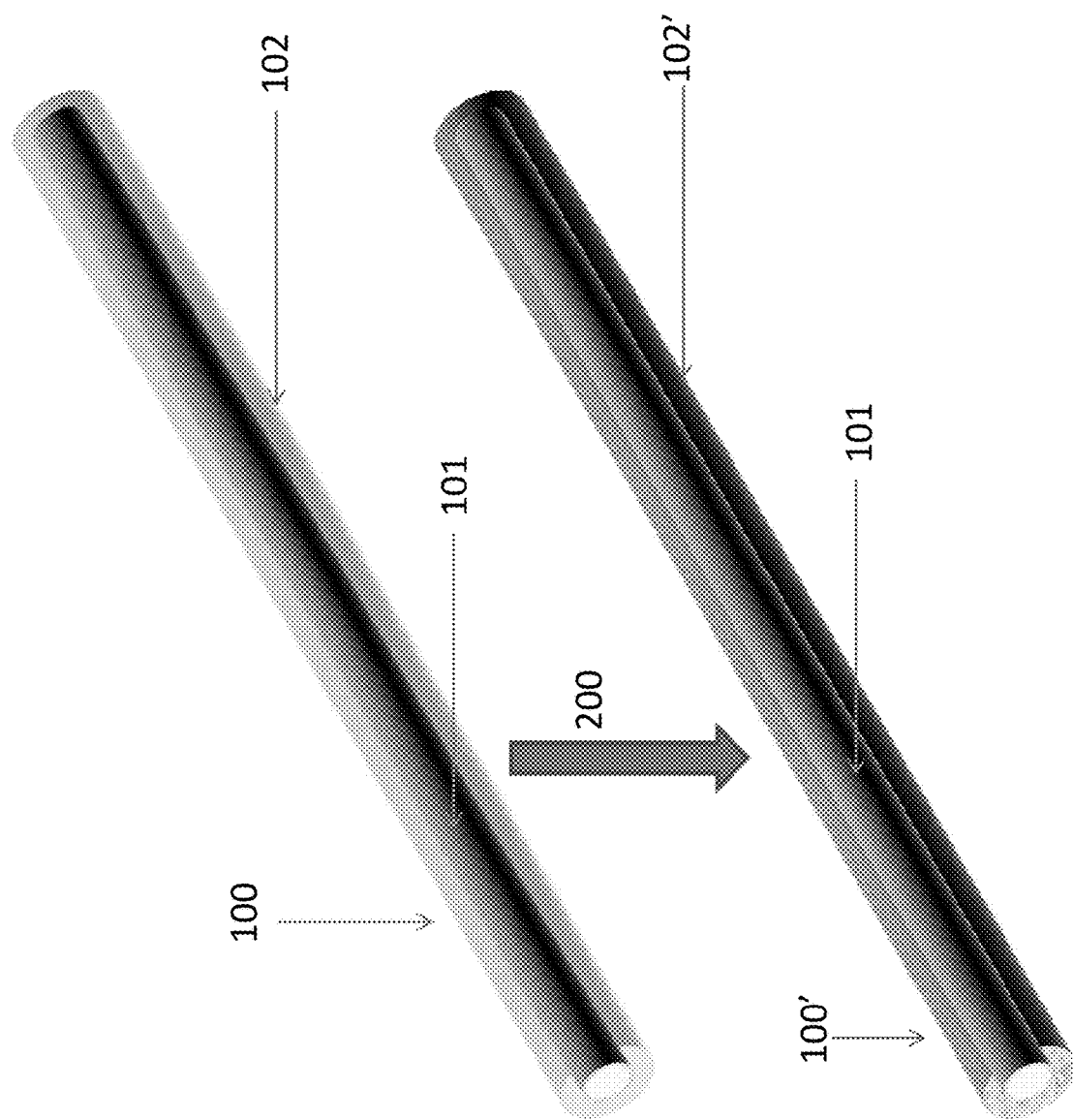
FIG. 2 shows the transformation of a core-shell nanofiber to a low friction nanofiber when hydrated.
Figure 3:
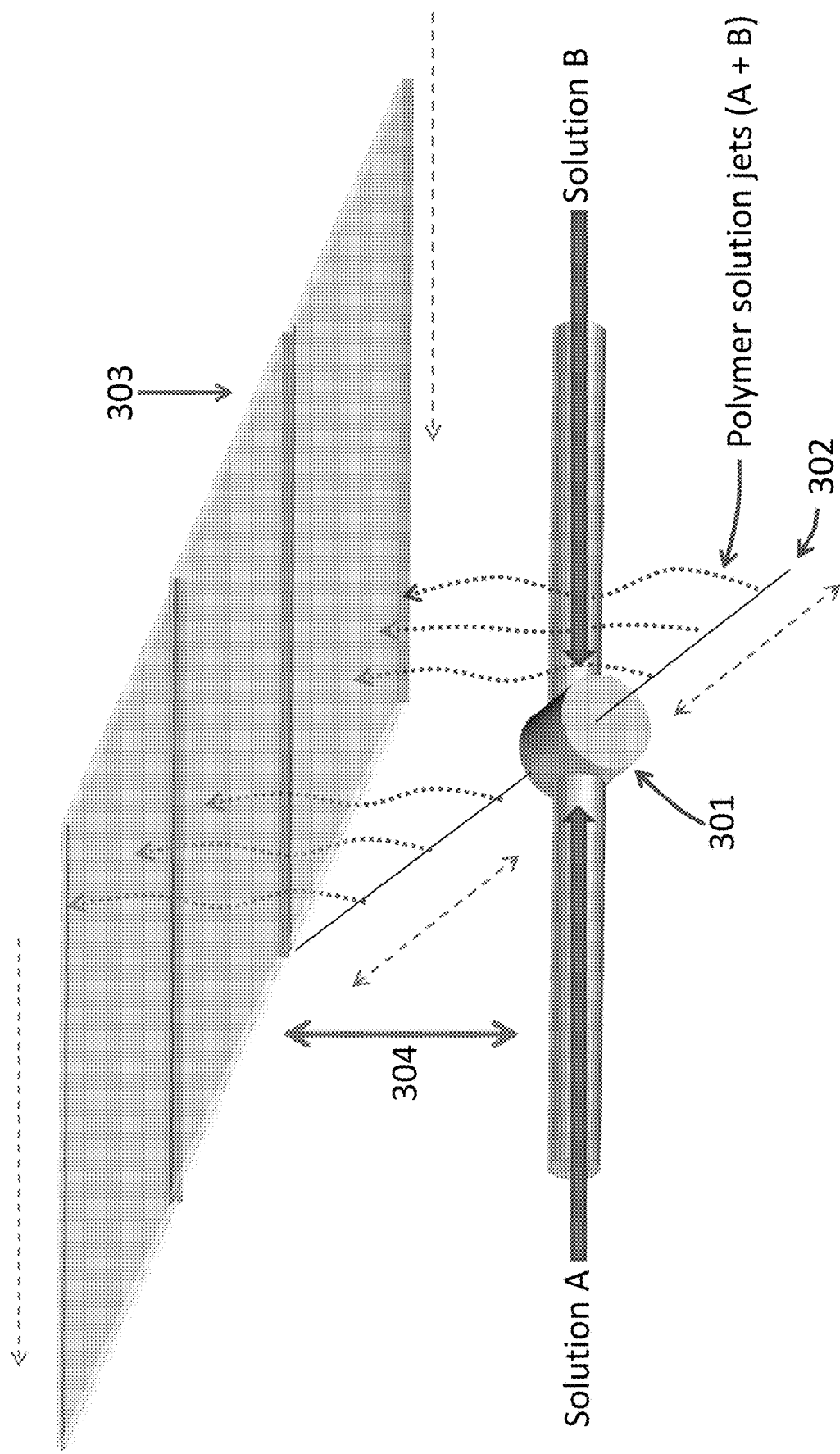
FIG. 3 shows the strategy for forming the core-shell nanofibers consisting of an active ingredient-loaded polymer matrix core and a layer of active ingredients surrounding the core.
Figure 4:
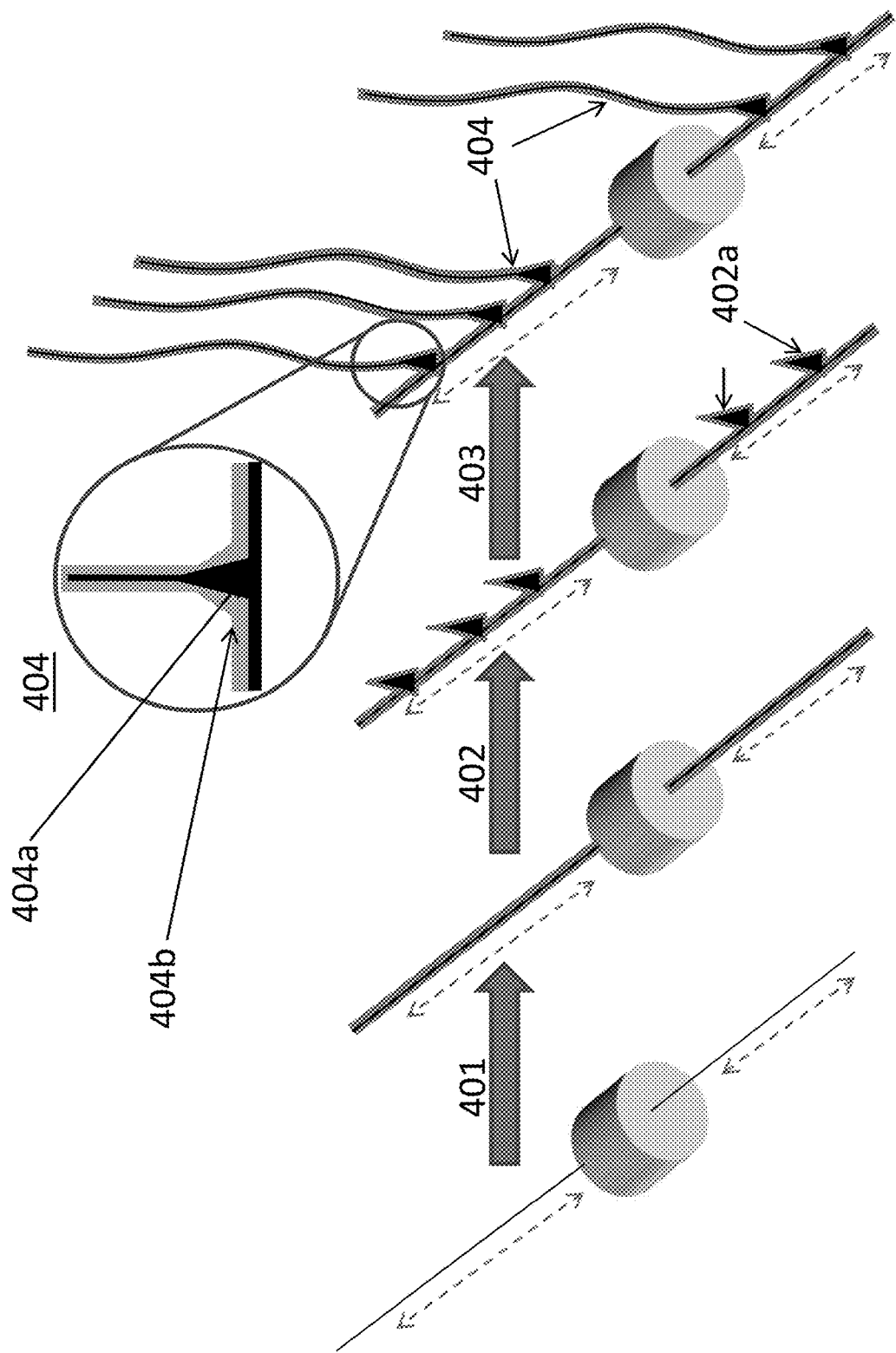
FIG. 4 shows the formation of cone-like structures and initiation of polymer jets.

References in the specification to "one embodiment", "an embodiment", "an example embodiment", etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt. % to about 5 wt. %, but also the individual concentrations (e.g., 1%, 2%, 3%, and 4%) and the sub-ranges (e.g., 0.1% to 0.5%, 1.1% to 2.2%, and 3.3% to 4.4%) within the indicated range.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

Definitions

The singular forms "a," "an" and "the" can include plural referents unless the context clearly dictates otherwise.

The term "about" can allow for a degree of variability in a value or range, for example, within 10%, or within 5% of a stated value or of a stated limit of a range.

The term "independently selected from" refers to referenced groups being the same, different, or a mixture thereof, unless the context clearly indicates otherwise. Thus, under this definition, the phrase "X1, X2, and X3 are independently selected from noble gases" would include the scenario where, for example, X1, X2, and X3 are all the same, where X1, X2, and X3 are all different, where X1 and X2 are the same but X3 is different, and other analogous permutations.

The term "skin mask" as used herein refers to but not limited to membrane, fibers, sheets (adhesive sheets, gel sheets, laminate sheets), gels, films, patches, masks, layers, multilayers, coatings, coverings, devices, articles, scaffolds or any composites thereof.

The term "active ingredients" as used herein refers to any compounds including plant extracts, vitamins, peptides, pharmaceutic drugs and any bioactive compounds that could alter the appearance of the skin and improve the skin conditions.

The term "free-surface electrospinning" or "needle-less electrospinning" as used herein refers to the technique of forming nanofibers without using needles or spinnerets. During "free-surface electrospinning" or "needle-less electrospinning", multiple jets can be initiated from a charged liquid surface, provided that the surface charge density is high enough and curvature can be introduced to the air-liquid interface. In one configuration, "free-surface electrospinning" or "needle-less electrospinning" can employ a magnetic liquid to create liquid "spikes" that perturbed the charged liquid surface. Other configurations include but not limited to liquid-filled trenches, slits, wetted spheres, rotating wires and fixed wires, cylinders, disks, conical wire coils, and gas bubbles rising through the liquid surface.

Description

The present invention provides a core-shell structured nanofiber consisting of an active ingredient-loaded polymer matrix core and a layer of active ingredient shell surrounding the core.

The electrospun fibers can be collected by substrates including but not limited to non-woven fabrics, cotton fabrics, silk fabrics, and Tencel fibrous fabrics.

The nanofiber-coated substrates can be trimmed into different shapes and sizes, thus forming different types of skin masks such as facial masks, eye masks, lip masks, neck masks and hand masks.

The active ingredients can be encapsulated into the electrospun fibers. The active ingredients can also be surface-attached onto the electrospun fibers. The active ingredients can be encapsulated into and surface-attached onto the electrospun fibers. The active ingredients can be physically trapped by the electrospun fibers. The active ingredients can also be chemically crosslinked to the electrospun fibers.

When the skin mask is used to cover the skin, the larger the fiber size, the less contact points between the mask and the skin, and the poorer conformation of the mask to the skin. On the other hand, the more contact points between the mask and the skin, the larger friction strength between the skin and the fibers when the skin mask is applied to the pre-moistened skin, the easier the mask gets torn open. Consequently the skin mask has to be thick enough (200-400 μm) so that the membrane has a certain level of mechanical strength to prevent any rupture occurrence. Microfiber membrane has less friction strength when applied to the pre-moistened skin but the conformation to the skin is poor.

When the core-shell nanofiber skin mask is used to cover the pre-moistened skin, the nanostructure of the mask allows the mask to adhere to the skin closely with more contact points than the microfiber mask. At the same time, the small molecules within the shell begin to dissolve when interacted with the water on the surface of pre-moistened skin. The dissolved small molecules can form a lubricating layer, thus allowing free shifting of the mask on the skin. Moreover, the lubricating layer contains highly concentrated active ingredient solution, leading to maximum diffusion of small molecules into the skin. A higher potential is thereby established in the skin for facilitating the subsequent delivery of active ingredients from the core in a controlled release manner.

The present invention also provides formulations and scalable methods for providing the skin mask described herein. More specifically, the present invention provides formulations and scalable methods for forming the low friction core-shell electrospun fibrous skin mask.

Polymer Solution for Electrospinning

A polymer, such as nylon, cellulose acetate (CA), polystyrene (PS), polyacrylonitrile (PAN), poly(lactic acid) (PLA), poly(lactic-co-glycolic acid) (PLGA), polybutylene terephthalate (PBT), polyurethane (PU), gelatin, chitosan or polyhydroxybutyrate-co-hydroxyvalerate (PHBV), is dissolved in an appropriate solvent, such as dimethylformamide (DMF), acetic acid (AA), formic acid (FA), dichloromethane (DCM), chloroform, acetone, 1,1,1,3,3,3-hexafluoro-2-propanol (HF2P), trifluoroacetic acid (TFA), 2,2,2-trifluoroethanol (TFE), or the combination thereof. Active ingredients, such as allantoin, bisabolol, dimethicone, ascorbic acid, kojic acid, hydroquinone, azelaic acid, niacinamide, vitamin E, retinoic acid, resveratrol, epigallocatechin-3 gallate (EGCG), lycopene, genistein or trehalose, is mixed with the polymer solution through gentle stirring using magnetic stirrer to form a homogenized emulsion or dispersion. The stirring speed is 200-800 rpm, such as about 400-600 rpm. The stirring and heating duration is 1-24 hours, such as about 4-6 hours. The viscosity of the polymer solution is 100-3000 cP, such as about 300-900 cP. The conductivity of the polymer solution is 10-100 μS/cm, such as about 20-40 μS/cm. The amount of polymer used in forming the polymer solution depends on the type of polymer selected and/or the corresponding solvent. In some embodiments, the weight percentage of the selected polymer in the polymer solution is in range of 2-30%. More preferably, the polymer is in a range of 5-25% w/w. In some preferred embodiments, the polymer is in a range of 8-20% w/w. For example, nylon is in a range of 10-15% w/w. Apart from polymer, it is possible that the core of the nanofiber of the present membrane comprises ceramic material(s), metal-based compound(s), polymer-ceramic composite(s), or any combination thereof to be incorporated with the active ingredients.

Working Conditions for Free-Surface Electrospinning

The low friction core-shell fiber layer is formed by free-surface electrospinning. The diameter of the stainless steel collecting electrode (CE, which the electrode a few centimeters above the moving substrate) is 0.1-0.3 mm, such as about 0.2 mm. The diameter of the stainless steel spinning electrode (SE) is 0.1-0.3 mm, such as about 0.2 mm. The sheet resistance of the antistatic spunbond substrate is $10^6$-$10^{12}$ Ω/sq, such as about $10^7$ Ω/sq. The distance between the CE and the substrate is 20-30 mm, such as about 25 mm. The distance between the SE and the substrate is 150-200 mm, such as about 180 mm. The applied voltage is 80-100 kV, such as about 80 kV. The current is 0.2-0.9 mA, such as about 0.4-0.5 mA. The temperature is 20-25° C., such as about 21-23° C. The relative humidity is 25-38%, such as about 30-35%. The substrate speed is 20-3000 mm/min, such as about 100 mm/min.

EXAMPLES

The embodiments of the present invention can be better understood by reference to the following examples which are offered by way of illustration. The present invention is not limited to the examples given herein.

Example 1

Preparation of Nylon/Ascorbic Acid Solution and Ascorbic Acid Solution

Nylon was dissolved in a mixture of acetic acid and formic acid (acetic acid:formic acid=2:1 by volume) at a concentration of 12% (w/w). Ascorbic acid was mixed with the nylon solution at a concentration of 10% (w/w). The mixture was stirred at 500 rpm for 24 hours at room temperature to form the nylon/ascorbic acid solution (namely, Solution A). The viscosity of the Solution A was 910 cP. The conductivity of Solution A was 50 μS/cm. Ascorbic acid solution (namely, Solution B) was made by a process that was similar to the process for making Solution A except that nylon was excluded. The viscosity of the Solution B was 1 cP. The conductivity of Solution B was 50 μS/cm.

Fabrication of Low Friction Core-Shell Electrospun Nylon/Ascorbic Acid Fibers

Figure 5B:
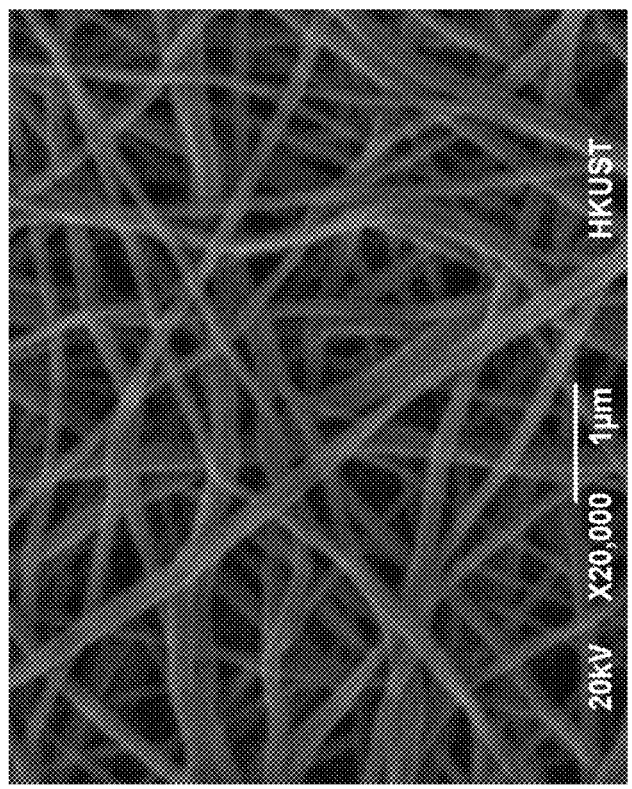
FIG. 5B shows the SEM micrograph of the core-shell nanofibers consisting of an ascorbic acid-loaded nylon core and a layer of ascorbic acid shell surrounding the core after soaking in water.
Figure 5A:
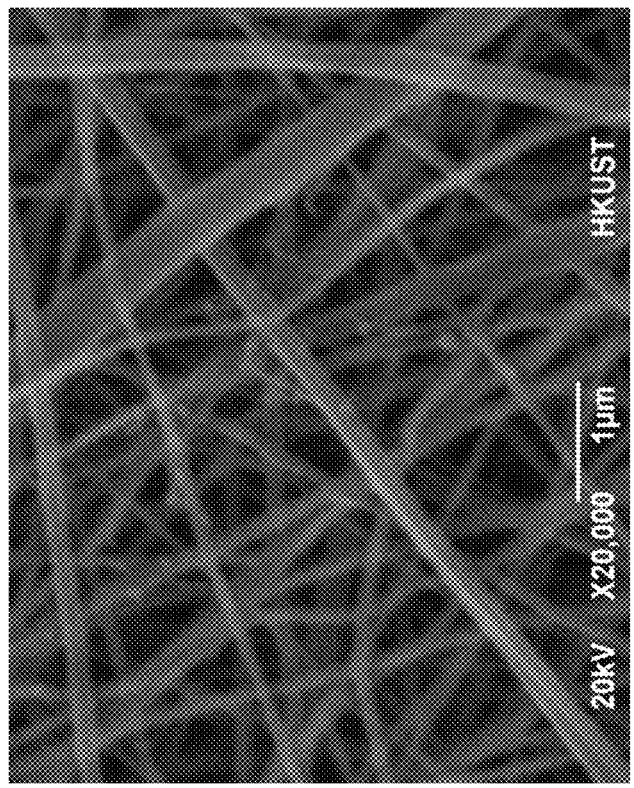
FIG. 5A shows the SEM micrograph of the as-spun core-shell nanofibers consisting of an ascorbic acid-loaded nylon core and a layer of ascorbic acid shell surrounding the core.

Low friction core-shell electrospun nylon/ascorbic acid fiber membrane was formed on cotton fibers as collecting substrate by free-surface electrospinning of Solution A and Solution B using the Nanospider (Elmarco, Czech Republic) together with a tailor-made external winding and unwinding system. The diameter of the stainless steel collecting electrode (CE) was 0.2 mm. The diameter of the stainless steel spinning electrode (SE) was 0.2 mm. The sheet resistance of the antistatic collecting substrate was $10^{10}$ Ω/sq. The distance between the CE and the substrate was 25 mm. The distance between the SE and the substrate was 180 mm. The applied voltage was 100 kV. The current was 0.5 mA. The temperature was 23° C. The relative humidity was 33%. The substrate speed was 100 mm/min Characterization FIGS. 5A and 5B show the SEM images of the electrospun nylon/ascorbic acid fibers before and after moisturized, respectively. The sheet resistance of the coating comprising electrospun nylon/ascorbic acid fibers is $10^{11}$ Ω/sq. The surface potential of the coating comprising nylon/ascorbic acid fiber is 20 V. The average diameter of the electrospun nylon/ascorbic acid fiber is 140 nm. The basis weight of the coating comprising the electrospun nylon/ascorbic acid fibers is 0.12 g/m².

Figure 6:
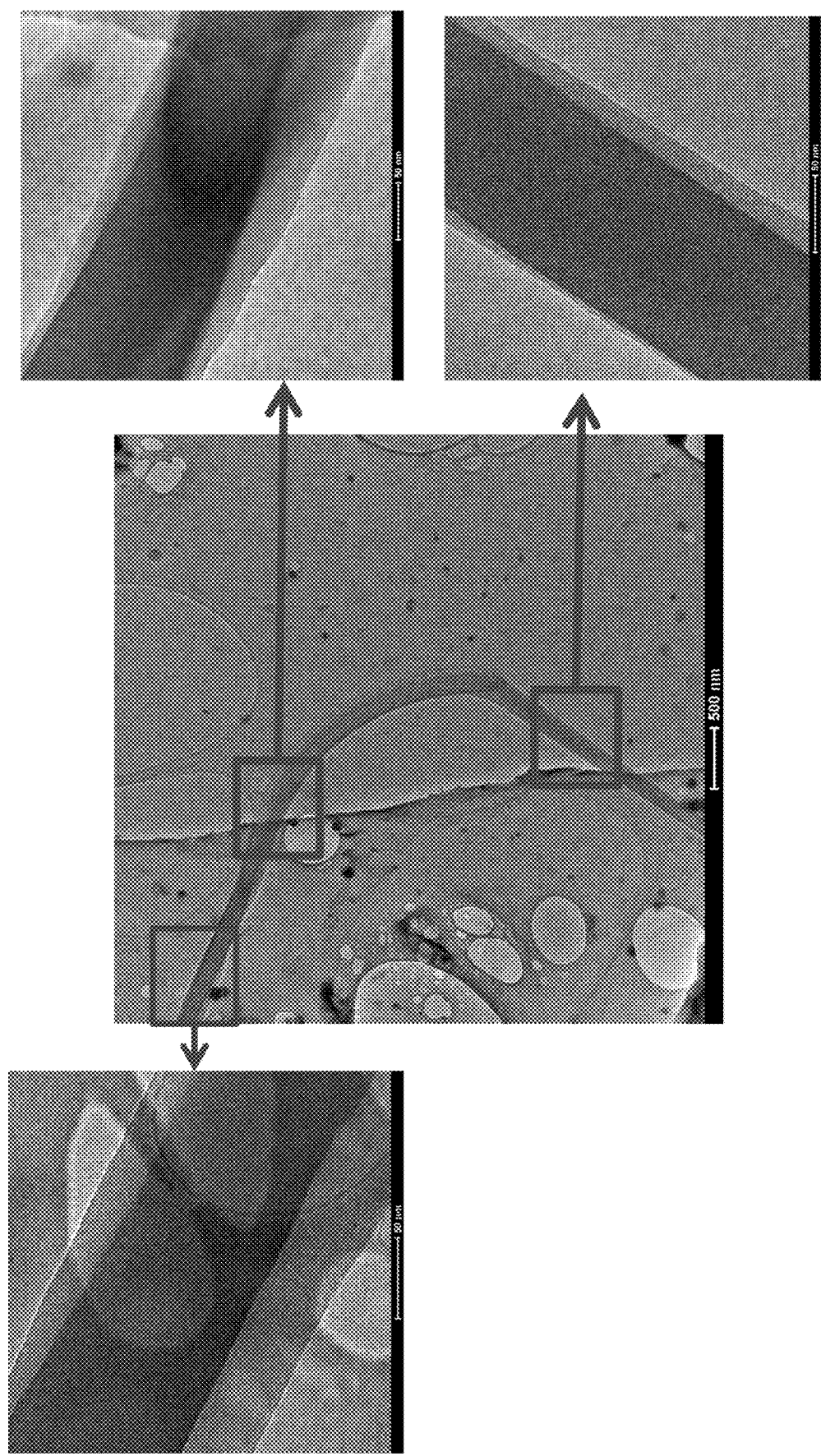
FIG. 6 shows the TEM image of a core-shell structured nanofiber consisting of an ascorbic acid-loaded nylon core and a layer of ascorbic acid shell surrounding the core.

The morphology of the core-shell fiber was observed via TEM. FIG. 6 demonstrates the core-shell structure of the nylon/ascorbic fibers. The average diameter of the core is 103 nm, and the average thickness of the shell is 43 nm.

The substrate with the coating comprising electrospun nylon/ascorbic acid fiber was packaged with the cover of another protective layer (pearl paper) into skin mask. The performance of this type of skin mask was assessed through two tests, namely, (1) Franz cell penetration test and (2) Friction strength test.

Penetration Test by Franz Cell

Penetration test was performed using Franz cell to evaluate the penetration percentage of ascorbic acid into the porcine ear skin model. Specifically, samples and controls were pre-loaded the same amount of active ingredients (i.e. ascorbic acid). The porcine skin samples were rinsed with distilled water and soaked in 0.9% NaCl solution. The top cell compartments of the Franz cell were soaked in distilled water for 5 minutes and then were filled with 0.9% NaCl solution with a temperature of 32° C. The porcine skin was placed on the Franz cell. Then the sample mask and control were placed on the porcine skin, respectively. The Franz cell was covered with the top cell compartment. After 15 min incubation, porcine skin under each sample were collected and minced. Ascorbic acid was then extracted and measured using the ascorbic acid assay kit. The penetration percentage of ascorbic acid was then determined.

The ascorbic acid skin penetration percentage for both the said low friction core-shell fiber mask and the control conventional skin mask having the same initial amount of ascorbic acid were assessed. The former skin mask comprising ascorbic acid-loaded nylon nanofibers resulted in 436% higher amount of ascorbic acid in the skin layer when tested with Franz cells in vitro when compared with the conventional skin mask without nanofiber.

Friction Strength Test

The friction strength test was performed to evaluate the friction strength between the fiber membrane and the skin. Prior to testing, the fiber membrane was pre-moistened and applied onto the porcine skin. A texture analyzer with tensile grip was employed to measure the tensile strength for shifting the fiber membrane along the skin at a constant rate 1 mm/s.

Core-shell fiber with nylon/ascorbic acid and non-core-shell fiber with nylon only were used for the friction strength testing. When the latter was applied to a wet skin, the shearing force was 1682 mN. However, when the former was applied to a wet skin, the shearing force was 207 mN.

Example 2

Preparation of Nylon/Urea Solution and Urea Solution

Nylon was dissolved in a mixture of acetic acid and formic acid (acetic acid:formic acid=2:1 by volume) at a concentration of 12% (w/w). Urea was mixed with the nylon solution at a concentration of 10% (w/w). The mixture was stirred at 500 rpm for 1 hour at room temperature to form the nylon/urea solution (namely, Solution C). The viscosity of Solution C was 800 cP. The conductivity of Solution C was 80 µS/cm. Urea solution (namely, Solution D) was made by a process that is similar to the process for making Solution C except that nylon was excluded. The viscosity of the Solution D was 1 cP. The conductivity of Solution D was 80 µS/cm.

Fabrication of Low Friction Core-Shell Electrospun Nylon/Urea Fibers

Figure 7B:
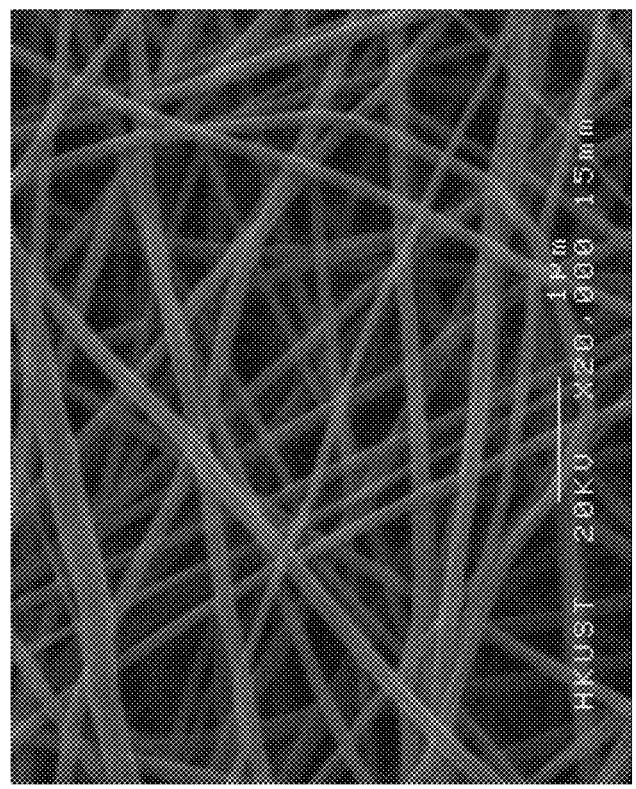
FIG. 7B shows the SEM micrograph of the core-shell nanofibers consisting of a urea-loaded nylon core and a layer of urea shell surrounding the core after soaking in water.
Figure 7A:
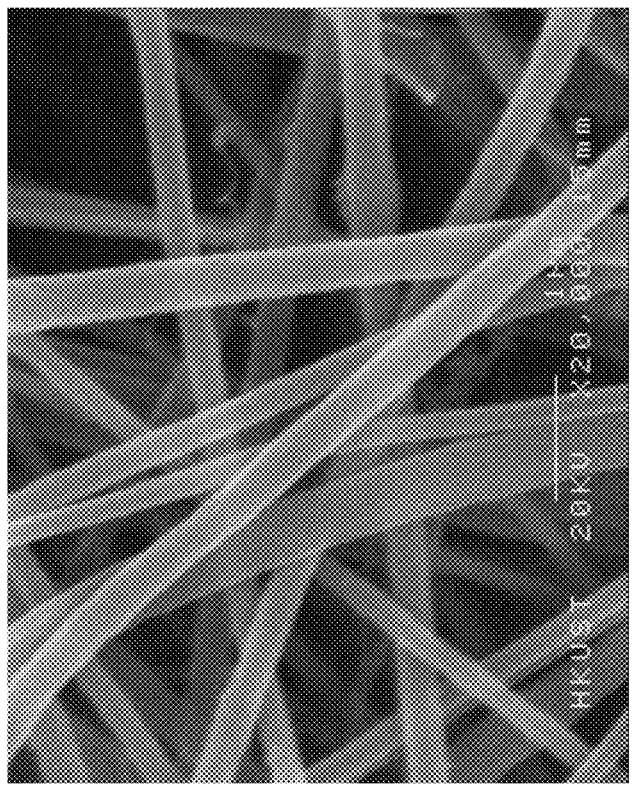
FIG. 7A shows the SEM micrograph of the as-spun core-shell nanofibers consisting of a urea-loaded nylon core and a layer of urea shell surrounding the core.

Low friction core-shell electrospun nylon/urea fiber membrane was formed on cotton fibers as collecting substrate by free-surface electrospinning of Solution C and Solution D using the Nanospider (Elmarco, Czech Republic) together with a tailor-made external winding and unwinding system. The diameter of the stainless steel collecting electrode (CE) was 0.2 mm. The diameter of the stainless steel spinning electrode (SE) was 0.2 mm. The sheet resistance of the antistatic collecting substrate was $10^{10}$ Ω/sq. The distance between the CE and the substrate was 25 mm. The distance between the SE and the substrate was 180 mm. The applied voltage was 100 kV. The current was 0.7 mA. The temperature was 23° C. The relative humidity was 33%. The substrate speed was 100 mm/min Characterization FIGS. 7A and 7B show the SEM images of the electrospun nylon/urea fibers before and after moisturized, respectively. The sheet resistance of the coating comprising electrospun nylon/urea fibers is $10^{11}$ Ω/sq. The surface potential of the coating comprising nylon/urea fiber is 20 V. The average diameter of the electrospun nylon/urea fiber is 220 nm. The basis weight of the coating comprising the electrospun nylon/urea fibers is 0.15 g/m².

Figure 8:
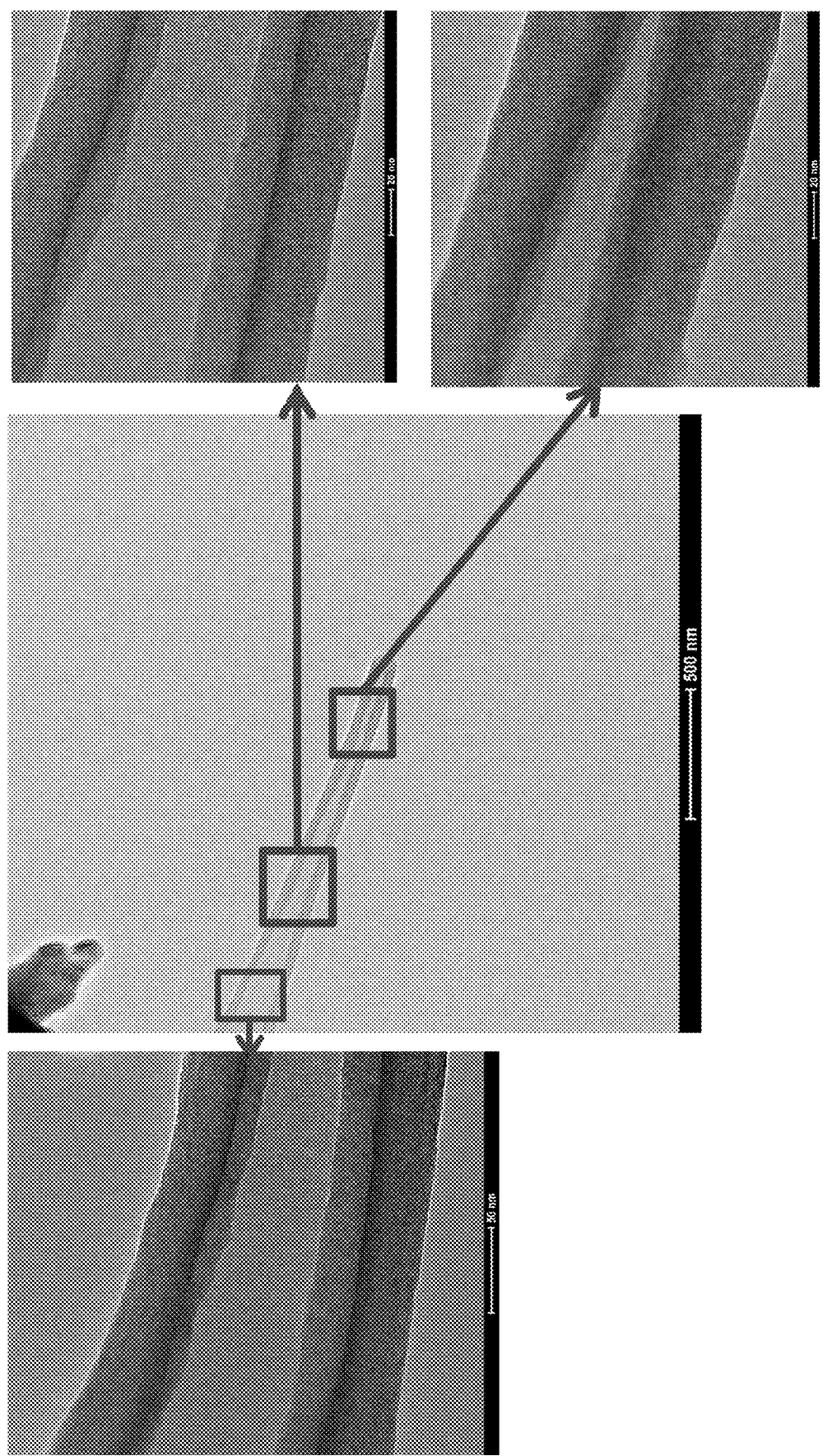
FIG. 8 shows the TEM image of a core-shell structured nanofiber consisting of a urea-loaded nylon core and a layer of urea shell surrounding the core.

The morphology of the core-shell fiber was observed via TEM. FIG. 8 demonstrates the core-shell structure of the nylon/urea fibers. The average diameter of the core is 144 nm, and the average thickness of the shell is 84 nm.

Penetration Test by Franz Cell

Penetration test was performed using Franz cell to evaluate the penetration percentage of urea into the porcine ear skin model. Specifically, samples and controls were pre-loaded the same amount of active ingredients (i.e. urea). The porcine skin samples were rinsed with distilled water and soaked in 0.9% NaCl solution. The top cell compartments of the Franz cell were soaked in distilled water for 5 minutes and then were filled with 0.9% NaCl solution with a temperature of 32° C. The porcine skin was placed on the Franz cell. Then the sample mask and control were placed on the porcine skin, respectively. The Franz cell was covered with the top cell compartment. After 15 min incubation, porcine skin under each sample were collected and minced. Urea was then extracted and measured using the urea assay kit. The penetration percentage of urea was then determined.

The urea skin penetration percentage for both the said low friction core-shell fiber mask and the control conventional skin mask having the same initial amount of urea were assessed. The former skin mask comprising urea-loaded nylon nanofibers resulted in 413% higher amount of urea in the skin layer when tested with Franz cells in vitro when compared with the conventional skin mask without nanofiber.

Friction Strength Test

The friction strength test was performed to evaluate the friction strength between the fiber membrane and the skin. Prior to testing, the fiber membrane was pre-moistened and applied onto the porcine skin. A texture analyzer with tensile grip was employed to measure the tensile strength for shifting the fiber membrane along the skin at a constant rate 1 mm/s.

Core-shell fiber with nylon/urea and non-core-shell fiber with nylon only were used for the friction strength testing. When the latter was applied to a wet skin, the shearing force was 1690 mN. However, when the former was applied to a wet skin, the shearing force was 216 mN.

Example 3

Fabrication of Fibers Having Urea-Loaded Nylon Core and Ascorbic Acid Shell

Figure 9B:
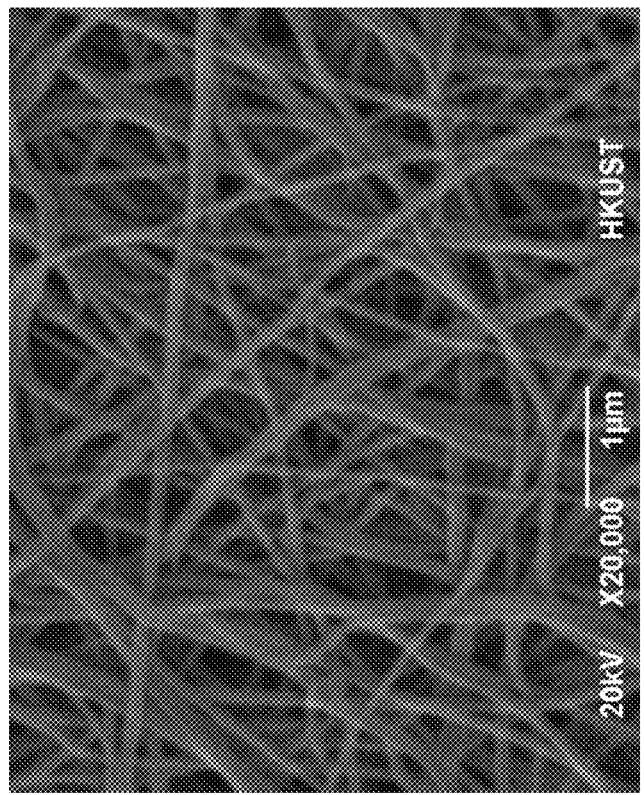
FIG. 9B shows the SEM micrograph of the core-shell nanofibers consisting of a urea-loaded nylon core and a layer of ascorbic acid shell surrounding the core after soaking in water.
Figure 9A:
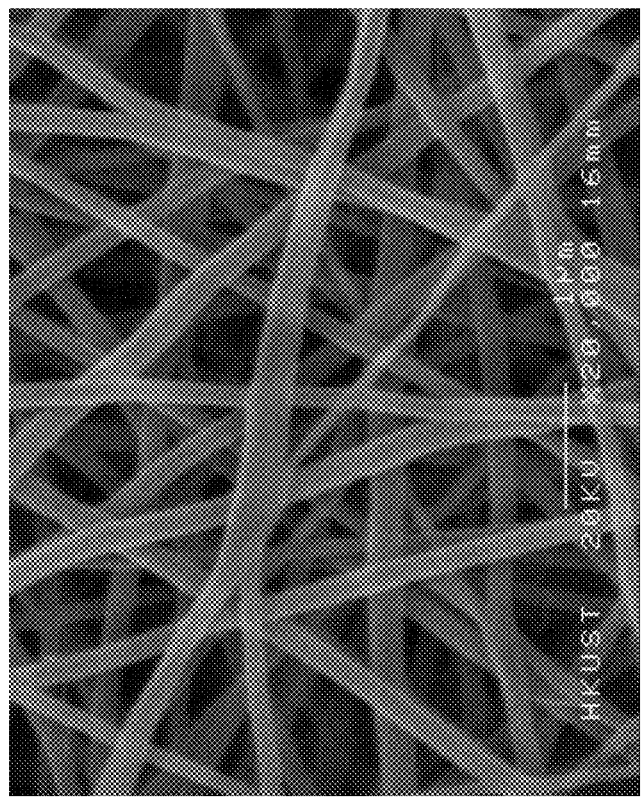
FIG. 9A shows the SEM micrograph of the as-spun core-shell nanofibers consisting of a urea-loaded nylon core and a layer of ascorbic acid shell surrounding the core.

Core-shell fibers having urea-loaded nylon core and ascorbic acid shell were formed on cotton fibers as collecting substrate by free-surface electrospinning of Solution B in Example 1 and Solution C in Example 2 using the Nanospider (Elmarco, Czech Republic) together with a tailor-made external winding and unwinding system. The diameter of the stainless steel collecting electrode (CE) was 0.2 mm. The diameter of the stainless steel spinning electrode (SE) was 0.2 mm. The sheet resistance of the antistatic collecting substrate was $10^{10}$ Ω/sq. The distance between the CE and the substrate was 25 mm. The distance between the SE and the substrate was 180 mm. The applied voltage was 100 kV. The current was 0.7 mA. The temperature was 23° C. The relative humidity was 33%. The substrate speed was 20 mm/min Characterization FIGS. 9A and 9B show the SEM images of the electrospun fibers having urea-loaded nylon core and ascorbic acid shell. The sheet resistance of the coating comprising electrospun fibers having urea-loaded nylon core and ascorbic acid shell is $10^{11}$ Ω/sq. The surface potential of the coating comprising fibers having urea-loaded nylon core and ascorbic acid shell is 20 V. The average diameter of the electrospun fibers having urea-loaded nylon core and ascorbic acid shell is 240 nm. The basis weight of the coating comprising the electrospun fibers having urea-loaded nylon core and ascorbic acid shell is 0.13 g/m².

Figure 10:
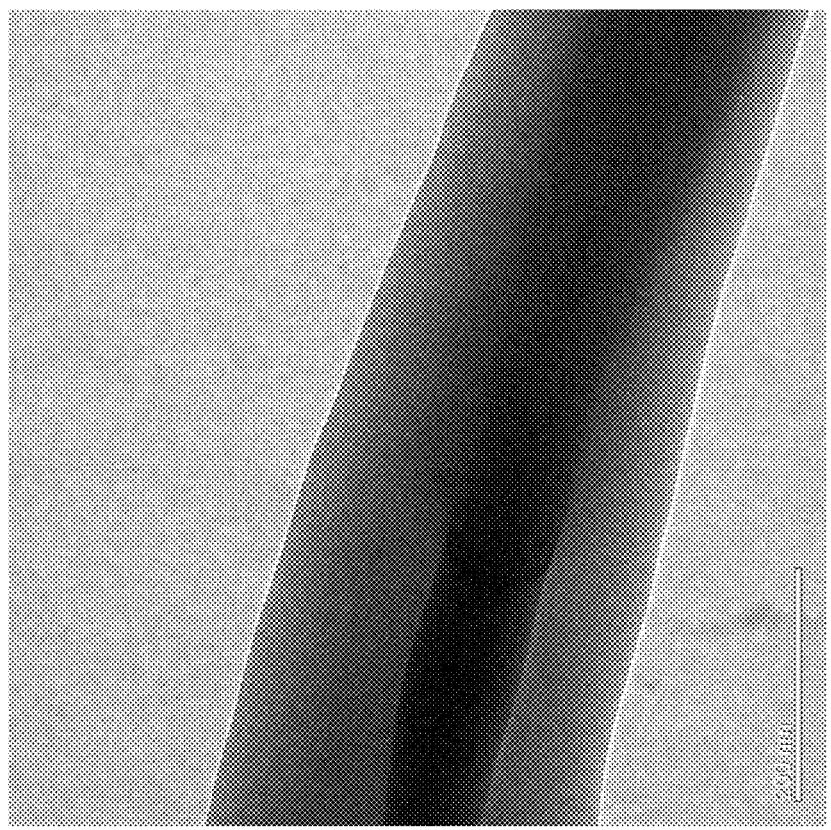
FIG. 10 shows the TEM image of a core-shell structured nanofiber consisting of a urea-loaded nylon core and a layer of ascorbic acid shell surrounding the core.

The morphology of the core-shell fiber was observed via TEM. FIG. 10 demonstrates the core-shell structure of the fiber having a urea-loaded nylon core and a layer of ascorbic acid shell surrounding the core. The average diameter of the core is 110 nm, and the average thickness of the shell is 98 nm.

In Vitro Release Studies

Figure 11:
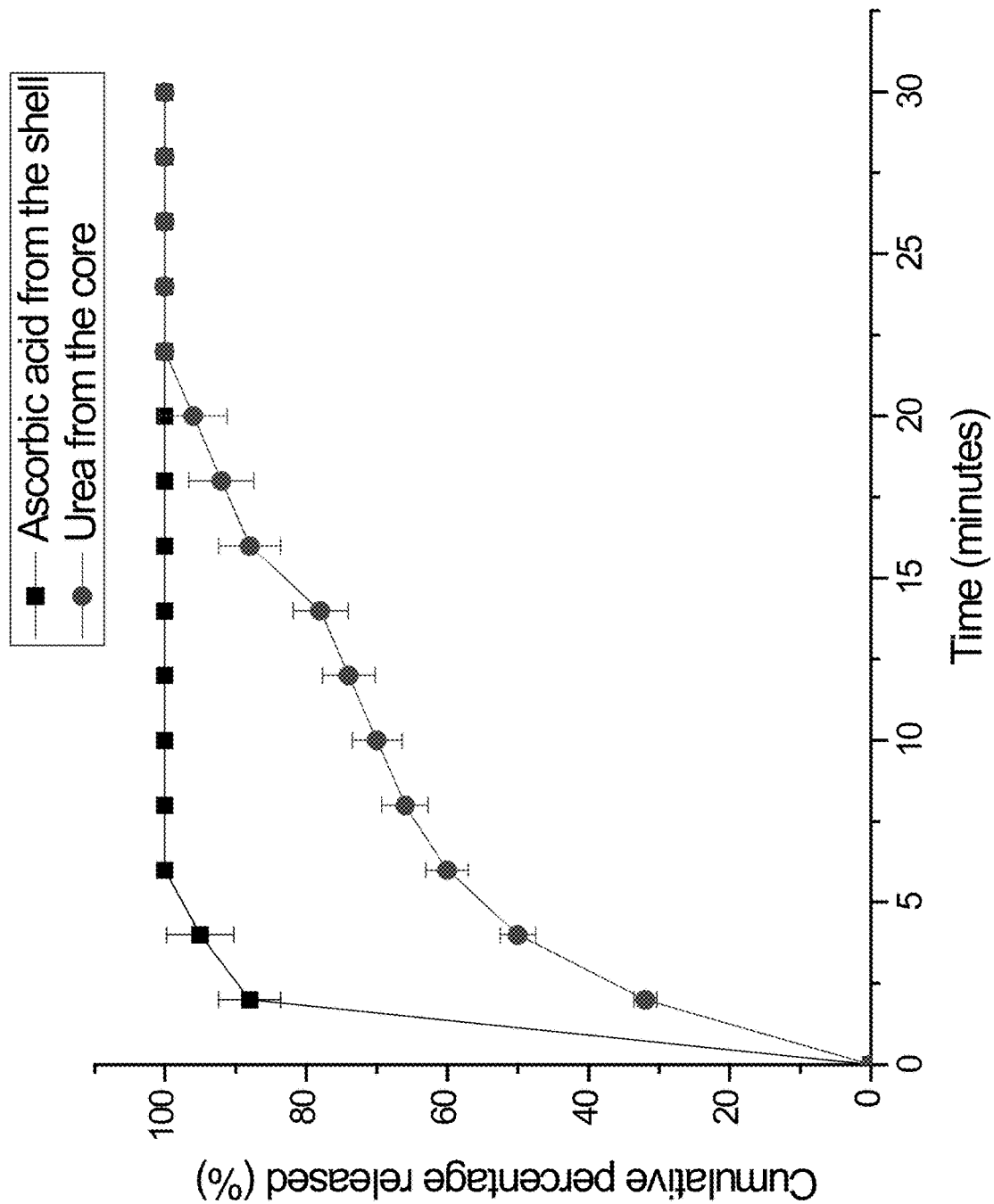
FIG. 11 shows the cumulative in vitro release curves of the membrane comprising core-shell nanofibers over a period of 30 minutes, said core-shell nanofiber is composed of an urea-loaded nylon core and a shell made of ascorbic acid only surrounding the core. The plot is presented in terms of the percentage mass released over the original mass of ingredient present.

Approximately 20 mg of fibrous membrane of Example 3 was added to a tube with 5 mL phosphate buffered saline (PBS), which was the release medium in the experiment. The resultant mixture was placed in a shaking water bath at 37° C. Two milliliters of sample mixture (one milliliter for urea assay and one milliliter for ascorbic acid assay) was extracted at specific time points (2, 4, 6, 8, 10, 12, 14, 16, 18, 20, 22, 24, 26, 28, 30 min) from each test tube. Two milliliters of PBS solution was then added to each mixture to make up 5 mL again and all the mixtures were incubated in the shaking bath again before the next set of sample mixtures were extracted. The urea assay kit and the ascorbic acid assay kit were used to test the concentrations of urea and ascorbic acid inside the PBS solutions respectively. The in vitro release of urea and ascorbic acid was carried out over a period of 30 minutes and the cumulative release curve was plotted, as shown in FIG. 11. Over 80% of ascorbic acid was released within 2 minutes while only around 30% of urea was released within the same period. Ascorbic acid was totally released within 6 minutes from the shell but it took around 22 minutes for complete release of urea from the core. The results demonstrate a sequential release of different ingredients (i.e. instant release of ascorbic acid from the shell and controlled release of urea from the core).

Example 4

Investigation into the Effect of Nanofibers on Rewet

Core-shell nanofibers of this example were fabricated using the method described in Example 3. The nanofibers were then incorporated into a superabsorbent polymer of diaper prototypes as acquisition layers. The absorption and rewet properties of the diaper incorporated with said nanofibers were evaluated as compared to diaper without said nanofibers as acquisition layers.

When synthetic urine was applied over the diaper with said nanofibers at the first time, rewet was reduced by 60% without affecting the absorption rate when compared with the same product without the said nanofibers.

When the same amount of synthetic urine was applied over the same type of diaper with the same type of nanofibers for 2 times, rewet was reduced by 45% without affecting the absorption rate when compared with the same product without the said nanofibers.

When the same amount of synthetic urine was applied over the same type of diaper with the same type of nanofibers for 3 times, rewet was reduced by 25% without affecting the absorption rate when compared with the same product without the said nanofibers.

What is claimed is:

1. A membrane comprising a plurality of randomly oriented core-shell nanofibers, each of said core-shell nanofibers comprising:
    a non-polymeric nanofiber shell which is composed of one or more active ingredients and remains intact under a dry condition but is instantly dissolvable under a wet condition; and
    a polymeric nanofiber core comprising a polymer incorporated with one or more active ingredients which remains intact under either a dry or wet condition but is able to release the one or more active ingredients in a controlled release manner when said nanofiber shell is dissolved;
    wherein the one or more active ingredients in any of the non-polymeric nanofiber shell and the polymeric nanofiber core are small molecules having a molecular weight of 400 Da or below; and
    wherein said membrane is shifted with a shearing force of 500 mN or below when the non-polymeric nanofiber shell of the membrane is substantially dissolved during contact with a wet skin.

2. The membrane of claim 1, wherein said core-shell nanofiber has a diameter of 100-1000 nm.

3. The membrane of claim 1, wherein the nanofiber core has a diameter of 50-900 nm.

4. The membrane of claim 1, wherein the nanofiber shell has a thickness of 25-250 nm.

5. The membrane of claim 1, wherein the core-shell nanofiber has a surface potential of 10-100 V.

6. The membrane of claim 1, wherein the small molecules have skincare properties comprising one or more of hydration, moisturizing, acne treatment, anti-irritation, whitening, anti-aging, and/or anti-oxidant.

7. The membrane of claim 6, wherein the small molecules having hydration and/or moisturizing properties comprise urea, pyrrolidone carboxylic acid (PCA), panthenol, trehalose, cyclomethicone, caprylyl glycol, lecithin, tocopheryl acetate, squalane, hydrolysed collagen, polyquaternium-51 and methyl gluceth-20.

8. The membrane of claim 6, wherein the small molecules having acne treatment property comprise alpha hydroxyl acid (AHA), salicylic acid, menthol and niacinamide.

9. The membrane of claim 6, wherein the small molecules having anti-irritation property comprise allantoin, bisabolol and dimethicone.

10. The membrane of claim 6, wherein the small molecules having whitening property comprise ascorbic acid, kojic acid, hydroquinone, azelaic acid and niacinamide.

11. The membrane of claim 6, wherein the small molecules having anti-aging property comprise vitamin E and retinoic acid.

12. The membrane of claim 6, wherein the small molecules having anti-oxidant property comprise resveratrol, epigallocatechin-3 gallate (EGCG), lycopene, genistein, and trehalose.

13. The membrane of claim 6, wherein the small molecules are incorporated into the polymeric core and interact with each other via hydrogen bonding or electrostatic attraction.

14. The membrane of claim 1, wherein the polymer of the polymeric core comprises nylon, cellulose acetate (CA), polystyrene (PS), polyacrylonitrile (PAN), poly(lactic acid) (PLA), poly(lactic-co-glycolic acid) (PLGA), polybutylene terephthalate (PBT), polyurethane (PU), gelatin, chitosan and polyhydroxybutyrate-co-hydroxyvalerate (PHBV).

15. The membrane of claim 1, wherein said membrane delivers small molecules of the active ingredients instantly when the non-polymeric nanofiber shell of the membrane is in contact with a wet skin and sequentially delivers said small molecules from the polymeric nanofiber core in a controlled release manner when the non-polymeric nanofiber shell is substantially dissolved to form a high concentration solution at the interface between the wet skin and the polymeric nanofiber core.

16. The membrane of claim 15, wherein the small molecules from both the non-polymeric nanofiber shell and polymeric nanofiber core are delivered transdermally into the wet skin.

17. A superabsorbent polymer of a diaper comprising the membrane of claim 1 as acquisition layers to reduce rewet amount by at least 25% as compared to the same type of superabsorbent polymer without said membrane.

18. The membrane of claim 1, wherein said core-shell nanofiber is prepared by:
mixing one or more active ingredients with a polymer solution to form a mixture and loading the mixture into a reservoir capable of moving back and forth through an electrode at high voltage;
loading an active ingredient solution containing at least one active ingredient into the same reservoir simultaneously with said mixture such that the electrode is coated with both the mixture and the solution;
placing a grounded moving substrate at a certain distance above the electrode such that an electric potential difference is created between the electrode and the substrate;
applying an electric force to the mixture and solution to form multiple cone-like structures along the electrode;
when the electric force is sufficient to overcome the surface tension of the mixture and the solution, a polymer jet is initiated from each cone-like structure, wherein the polymer jet is a coaxial structure comprising an active ingredient-loaded polymer solution core and an active ingredient solution shell surrounding the core;
evaporating the solvent of the mixture and the solution such that a plurality of the polymer jets solidifies and forms core-shell nanofibers; and
collecting said core-shell nanofibers on the moving substrate.

* * * * *